United States Patent [19]

Burns et al.

[11] Patent Number: 5,486,476
[45] Date of Patent: Jan. 23, 1996

[54] LIPOPROTEIN (A) PEPTIDES AND THEIR USE

[75] Inventors: Geoffrey Burns, Munich; Wolf-Deiter Engel, Feldafing; Christoph Seidel, Weilheim, all of Germany

[73] Assignee: Boehringer Mannheim GmbH, Mannheim, Germany

[21] Appl. No.: 196,940

[22] Filed: Feb. 9, 1994

[30] Foreign Application Priority Data

Feb. 9, 1993 [DE] Germany ............ 43 04 638.4

[51] Int. Cl.$^6$ .................. G01N 31/00; A61K 38/04; C07K 7/00
[52] U.S. Cl. .................. 436/15; 530/324; 530/326; 530/327; 530/328; 530/329; 530/334
[58] Field of Search .................. 530/326, 327, 530/328, 329, 324, 334; 436/15

[56] References Cited

U.S. PATENT DOCUMENTS 4,945,040  7/1990  Fless et al. .................. 435/7

FOREIGN PATENT DOCUMENTS 0327418    8/1989   European Pat. Off..
WO92/09893 6/1192   WIPO.
WO94/04563 3/1994   WIPO.

OTHER PUBLICATIONS

H–C Guo, et al, *Journal of Lipid Research*, "Characterization of Five Mouse Monoclonal Antibodies to Apolipoprotein [A] . . . " vol. 30, No. 1, Jan. 1989, pp. 23–27.

*Primary Examiner*—Jill Warden
*Assistant Examiner*—Benet Prickril
*Attorney, Agent, or Firm*—Nikaido, Marmelstein, Murray & Oram

[57] ABSTRACT

The invention concerns peptides which have a partial sequence of lipoprotein (a) as well as their use for the purification of antibodies by means of affinity chromatography, as an immunogen for the production of antibodies and as a standard in an immunological test or as a competitive hapten in an agglutination test.

9 Claims, No Drawings

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 1:

Gln Ala Pro Thr Glu Gln Arg Pro Gly Val Gln Glu
    1                5                        10

( 2 ) INFORMATION FOR SEQ ID NO: 2:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 2:

Ser Tyr Arg Gly Thr Tyr Ser Thr Thr Val Thr Gly Arg
    1                5                        10

( 2 ) INFORMATION FOR SEQ ID NO: 3:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 3:

```
Arg  Thr  Pro  Glu  Tyr  Tyr  Pro  Asn  Ala  Gly  Leu  Ile
1                  5                       10
```

( 2 ) INFORMATION FOR SEQ ID NO: 4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 4:

```
Pro  Asp  Ala  Val  Ala  Ala  Pro  Tyr
1                  5
```

( 2 ) INFORMATION FOR SEQ ID NO: 5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 5:

```
Cys  Ser  Asp  Ala  Glu  Gly  Thr  Ala  Val  Ala
1                  5                       10
```

( 2 ) INFORMATION FOR SEQ ID NO: 6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 6:

```
Thr  Pro  Val  Pro  Ser  Leu  Glu
1                  5
```

( 2 ) INFORMATION FOR SEQ ID NO: 7:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 7:

```
Leu  Glu  Thr  Pro  Thr  Val  Val  Pro  Val  Pro  Ser
1                  5                       10
```

( 2 ) INFORMATION FOR SEQ ID NO: 8:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO: 8:

Thr  Phe  Ile  Pro  Gly  Thr  Asn  Lys
1                      5

LIPOPROTEIN (A) PEPTIDES AND THEIR USE

The invention concerns peptides which have a partial sequence of lipoprotein (a) as well as their use for the purification of antibodies by means of affinity chromatography, as an immunogen for the production of antibodies and as a standard in an immunological test or as a competitive hapten in an agglutination test.

An increased concentration of lipoprotein (a) (Lp(a)) represents a risk factor for cardiac infarction or stroke independent of the LDL concentration (H. -C. Guo et al., Journal of Lipid Research 30 (1989), 23–37). The significance of this risk factor for diagnostics is in particular that the Lp(a) concentration is not influenced by dietary habits or therapy with hydroxy-methylglutaryl-CoA reductase inhibitors so that an important indication for a genetic disposition for cardiac infarction or stroke can be obtained via the determination of the Lp(a) concentration (C. Labcur et al., Clinical Chemistry 35 (1989), 1380–1384). However, the specific diagnostic detection of Lp(a) is made difficult due to the fact that Lp(a) is, on the one hand very similar to LDL with respect to its high content of cholesterol esters and the component apoprotein B100 and on the other hand apoprotein (a), which distinguishes Lp(a) from LDL, shows a very high homology to plasminogen (H. -C. Guo et al., Journal of Lipid Research 30 (1989), 23–37). Antisera obtained by immunization with Lp(a) therefore do not only react with Lp(a) but to a substantial extent also with LDL and/or plasminogen.

In order to still detect Lp(a) as specifically as possible, antisera against Lp(a) were purified by a time-consuming immunoadsorptive purification on LDL, Lp(a) or apolipoprotein (a) (Kraft et al., Arteriosclerosis 8 (1988), 212–216). In addition it was attempted to achieve a specific Lp(a) test by means of a special ELISA test procedure (Fless et al., Journal of Lipid Research 30 (1989), 651–662). In this process an antibody against apolipoprotein (a) is for example used to immobilize Lp(a) to be detected from the sample and an antibody against apolipoprotein B100 is used to detect immobilized Lp(a). However, these methods are very time-consuming. Moreover, at the physiological concentrations of Lp(a) (up to more than 1 mg/ml), a high (100- to 1000-fold) sample dilution is necessary for a determination according to the ELISA principle which is very susceptible to interference.

The object of the invention was therefore to provide a simpler purification of antibodies against Lp(a) as well as a reliable detection method for the specific determination of Lp(a).

This object is achieved by a peptide which contains one of the sequences shown in SEQ ID NO: 1–8 and which shows a negative band between 190 and 200 nm in the CD spectrum. Peptides which only contain part of the sequences shown in SEQ ID NO: 1–8 and which bind in an analogous way are also suitable according to the invention. However, the minimum length of such peptides is four amino acids.

The total length of the peptides is uncritical provided they are present in a random coil structure. However, it is usually not advantageous to use peptides which are longer than 50 amino acids since then the synthesis becomes more time-consuming and heterogeneous, undefined mixtures of peptides of various lengths are formed. Peptides with a length of 4 to 20 amino acids are preferably used.

For the suitability of peptide antigens according to the invention it is essential that they are not present in a defined folded structure but in a linear form. Such a linear structure is also denoted random coil structure. CD spectroscopy may be used to examine whether an oligopeptide has such a structure. A peptide with random coil structure has a negative band between 190 and 200 nm in the CD spectrum (cf Ann. Rev. Biophys. Chem. 17 (1988), 145–166).

The peptides according to the invention are produced synthetically in a known manner, preferably by means of fluorenyl-oxycarbonyl solid phase synthesis.

It surprisingly turned out that the use of these peptides enables antibodies against Lp(a) which only have a low reactivity with LDL and/or plasminogen to be obtained in a single step by means of affinity chromatography. In this connection the term low reactivity is understood to mean that the cross-reactivity with LDL and/or plasminogen is at most 1.0 % relative to the reactivity with Lp(a).

Therefore the invention in addition concerns (a) the use of a peptide according to the invention for the purification of antibodies against Lp(a) by means of affinity chromatography in which the peptide is bound to a carrier material on which the antibody can then be purified in a known manner by means of affinity chromatography respectively (b) a method for the purification of antibodies against Lp(a) by means of affinity chromatography in which the peptide is bound to a carrier material on which the antibody can then be purified in a known matter by means of affinity chromatography.

All carrier materials which are usually used in affinity chromatography can be used as the carrier material, Sepharose-AH (Pharmacia LKB) or Affi-Gel 10 (BioRad) are preferably used. In this process binding of the peptide to Sepharose-AH is carried out in a known way by activating the peptide with maleinimidobenzoyl-N-hydroxy-succinimide ester (MBS) or glutaraldehyde. Binding to Affi-Gel 10 does not require an activation of the peptide and is carried out according to the manufacturer's instructions. Purification of the antiserum by means of the affinity chromatography matrix obtained in this way is carried out in a known way by application of the antiserum, washing with a buffer of a high ionic strength and subsequent elution with a buffer of a low ionic strength and a pH value below 5. It is preferably washed with PBS (according to Dulbecco and Vogt, J. Exp. Med. 99 (1954), 167–182)/0.5 mol/l sodium chloride and eluted with 0.2 mol/l glycine HCl pH 2.6. The antibodies obtained in this way only show a low reactivity with LDL and plasminogen.

In addition the peptides according to the invention are suitable as an immunogen or hapten for the production of antibodies against Lp(a) which only have a low reactivity with LDL and/or plasminogen.

Therefore the invention also concerns (a) the use of a peptide according to the invention as an immunogen for the production of antibodies against Lp(a) which only have a low reactivity with LDL and/or plasminogen respectively (b) a method for the production of antibodies against Lp(a) which only have a low reactivity with LDL and/or Plasminogen in which a peptide according to the invention is used as an immunogen. In this process the peptides can be used as such for the immunization or bound to a carrier molecule. The immunization is carried out in a known way in the animals usually used for this for example as described in U.S. Pat. No. 4,478,744. Rabbits, goats, rats, sheep or, for the production of monoclonal antibodies, mice are preferably used. The antiserum obtained can preferably be purified as described above by affinity chromatography. For the production of monoclonal antibodies the spleen cells of the immunized animals are immortalized according to known methods and those immortalized cells whose culture supernatant contains an antibody against Lp(a) are cloned. Whether a culture supernatant has an antibody against Lp(a) is determined in the usual manner by means of an ELISA test.

A further advantage of the peptides according to the invention is that they can be obtained in large amounts in a uniform composition.

Therefore they are better suited as a standard for quantitative determinations of Lp(a) than the very non-uniform material isolated from natural sources.

Therefore a further object of the invention is the use of a peptide according to the invention as a standard in an immunological test for the quantitative determination of Lp(a). The immunological determination of Lp(a) can in this case be carried out according to all known methods. In certain cases such as e.g. in non-competitive test systems it is necessary to bind several peptides according to the invention having the same or different sequences to a carrier molecule.

In addition the present invention concerns the use of a peptide according to the invention as a hapten in a competitive immunological test. For this the peptides according to the invention are preferably biotinylated, bound to a solid phase coated with streptavidin and the competitive test is carried out in the usual manner according to the ELISA principle. However, in a competitive test according to the ELISA principle the peptide according to the invention can also be bound to the label (enzyme, fluorescent label).

However, in the case of an immunoassay based on the ELISA principle it is necessary to carry out a high and thus time-consuming sample predilution which is susceptible to mistakes when Lp(a) is at physiological concentrations. The turbidimetric method of determination (TINIA=turbidimetric inhibition immunoassay) which is more suitable in this case with regard to its concentration range has up to now been hindered by the fact that Lp(a) generates adequate turbidity signals with polyclonal as well with monoclonal antibodies only under certain conditions. Such an adequate turbidity can, however, be achieved when one or several peptides according to the invention are coupled to a carrier and the complex obtained is used as a hapten in an agglutination test. This turbidity is then reduced by the analyte to be determined in an amount proportional to the amount of analyte. 30 to 40 peptide molecules are preferably coupled per carrier molecule. Binding of the peptide according to the invention to the carrier can in this case be achieved directly via covalent bonds or also indirectly e.g. by biotinylating the peptide and coating the carrier material with streptavidin. Proteins such as immunoglobulins, albumin, β-galactosidase, polymers such as aminodextrans or polylysines or particles such as latex or gold are preferably used as the carrier molecule either alone or in combination with one another. Coupling to the carrier molecule is achieved in a known way e.g. using reagents such as glutaraldehyde, ethyldimethylaminopropylcarbodiimide, maleimidohexanoic acid-N-hydroxysuccinimide ester or other known homo and heterobifunctional linkers.

Therefore the invention also concerns the use of a peptide according to the invention as a Lp(a) hapten in an agglutination test for the determination of Lp(a) in which at least one peptide according to the invention is bound to a carrier so that an agglutinate forms when the complex which is formed in this way is incubated with an antibody which recognizes the respective Lp(a) hapten, the formation of which is decreased in the presence of free Lp(a) from the sample.

The present invention finally concerns a method for the immunological determination of Lp(a) via a competitive agglutination test by incubating a carrier-bound Lp(a) hapten with an antibody against this hapten and with the sample to be analysed and measuring the measured signal which occurs in this process in the presence and absence of the sample to be analysed whereby the carrier-bound Lp(a) hapten contains at least one peptide according to the invention.

The agglutination test in this process is carried out in a well-known manner. For this the carrier-bound Lp(a) hapten is for example firstly incubated with an antibody which recognizes this hapten and thus forms a complex with the carrier-bound Lp(a) hapten, which leads to a certain measured signal which is usually a certain turbidity of the reagent solution. After addition of the sample to be analysed, free Lp(a) from this sample competes with the carrier-bound Lp(a) hapten for binding to the antibody and thus reduces the aggregation of the carrier-bound Lp(a).hapten by the antibody and thus the turbidity. The measured decrease in turbidity is compared to the decrease in turbidity which is obtained by addition of known amounts of a Lp(a) standard and the amount of Lp(a) in the sample to be analysed is determined from this comparison. A peptide according to the invention is preferably used as this standard. Apart from this the agglutination test can also be carried out according to other methods for a competitive test procedure familiar to a person skilled in the art. The carrier-bound Lp(a) hapten can for example also be simultaneously incubated with the sample and the antibody during which free Lp(a) from the sample competes with the carrier-bound hapten for binding to the antibody, so that the observed agglutination is inversely proportional to the amount of free Lp(a) in the sample. A further possibility is to firstly incubate the antibody with the sample by which means an amount of antibody corresponding to the amount of free Lp(a) in the sample is bound. After incubation with the carrier-bound Lp(a) hapten an agglutination occurs which is directly proportional to the amount of free Lp(a) in the sample.

In this process the Lp(a) concentration is determined on a molar basis (by using a peptide which only occurs once in Lp(a) e.g. the peptide shown in sequence SEQ ID NO 8) or on a mass basis (when using a peptide which occurs several times per Lp(a) molecule e.g. the peptides having the sequences shown in SEQ ID NO 1–7).

In addition the invention concerns a method for the immunological determination of Lp(a) by incubating a Lp(a) hapten bound to a label with an antibody against this hapten and the sample to be analysed and measuring the measured signal which occurs in this way in the presence and absence of the sample to be analysed which is characterized in that the Lp(a) hapten bound to the label contains at least one peptide according to the invention. All labels which are usually used can be used as labels in this process, such as enzymes, enzyme fragments, chemiluminescent or fluorescent dyes and radioactive isotopes. The immunological determination can be carried out according to U.S. Pat. No. 5,229,073. The determination is preferably carried out according to the FPIA, EMIT or CEDIA (U.S. Pat. No. 4,708,929) principle.

In the fluorescence polarization immunoassay (FPIA) the hapten is labelled with a fluorescent substance. These molecules absorb light energy and release it again in a period of about $10^{-8}$ sec as light of a longer wavelength. If the fluorophore is excited by polarized light, the degree of polarization of the emitted light depends on the speed of rotation of the tracer (analyte-fluorophore conjugate). Binding of the tracer to an antibody hinders the rotation of the fluorophore. The free tracer rotates faster and depolarizes the excitatory light more than the larger, more inert antibody-tracer complex.

The more analyte is present in the sample the less antibody-tracer complexes form and the less fluorescence polarization can be measured (W. Dandliker et al., Journal of Exp. Med. 122 (1965), 1029).

In the enzyme multiplied immunoassay technique (EMIT) the hapten to be detected is covalently coupled to the marker enzyme in such a way that the enzymatic activity is retained. However, after an antibody binds to the hapten part, the substrate binding to the enzyme is sterically hindered so that no enzymatic conversion of the substrate can take place. As in the CEDIA principle, the antigen from the sample solution to be determined also displaces the antibody from the enzyme-bound hapten in this case and thus enables an enzymatic activity which is proportional to the concentration of the antigen to be analysed in the sample solution (Gunzer et al., "Kontakte III", 1980, 3–11 and K. Rubenstein, Biochemical and Biophysical Research Communications 47 (1972), 846–851).

In the CEDIA principle, the antigen alone from the sample to be analysed effects the association of inactive enzyme acceptor and inactive enzyme donor to form an active enzyme whose activity is thus proportional to the amount of antigen in the sample to be analysed (Henderson et al., Clinical Chemistry 32 (1986), 1637–1641). In this case certain enzymes such as e.g. β-galactosidase are used for the detection which are each present as two enzymatically inactive components, namely a large polypeptide (enzyme acceptor) and a small polypeptide (enzyme donor), and these components spontaneously associate to form an enzymatically active protein. The hapten to be detected as the analyte is bound to the enzyme donor in such a way that the association of the enzyme donor with the enzyme acceptor to form the active enzyme is not impaired by this binding. This association is, however, impaired when an antibody against the antigen binds to the antigen-enzyme donor complex. Therefore no active enzyme can be formed in a reagent solution in which enzyme acceptor, antigen-enzyme donor complex and the corresponding antibody are present and no enzymatic activity is measured. After addition of the sample solution, the antigen from this sample solution then displaces the antibody from the binding to the antigen-enzyme donor complex and thus enables the formation of the active enzyme.

The antibodies produced by a method for the purification of antibodies against Lp(a) by means of affinity chromatography in which the peptide is bound to a carrier material on which the antibody can then be purified in a known matter by means of affinity chromatography or a method for the production of antibodies against Lp(a) which only have a low reactivity with LDL and/or Plasminogen in which a peptide according to the invention is used as an immunogen are especially suitable in an immunological method for the detection of Lp(a). Therefore the invention concerns also the use of these antibodies according to the invention in an immunological method for the detection of Lp(a).

The invention is elucidated further by the following examples together with the sequence protocols 1–8 which give the sequences of the peptides according to the invention.

EXAMPLE 1

Peptide Synthesis

The peptide having the sequence SEQ ID NO 1 which is extended by a C-terminal Cys is produced by means of fluorenyloxycarbonyl(Fmoc) solid phase synthesis. The reactions are carried out on a Labortec SP 640 peptide synthesizer (Labortec, Switzerland). In this case synthesis is carried out on 5 g Wang resin (polystyrene/1% divinylbenzene) with a peptide loading of 0.5 mmol/g (analogous to JACS 95 (1973), 1328). Coupling is achieved by incubating the resin with the corresponding Fmoc-amino acid derivative (1 equivalent) as well as 1.2 equivalents dicyclohexylcarbodiimide and 1.1 equivalents N-hydroxybenzotriazole for 90 min. at room temperature in dimethylformamide as reaction medium. 4 equivalents of each of the Fmoc-amino acid derivatives in relation to 1 mol anchor group are used in the following order: glutamine (with trityl protecting group), alanine, proline, threonine (with tert. butyl protecting group), glutamic acid (with tert. butyl ester protecting group), glutamine (with trityl protecting group), arginine (with pentamethylchromium protecting group), proline, glycine, valine, glutamine (with trityl protecting group), glutamic acid (with tert. butyl ester protecting group) and cysteine (with trityl protecting group). The coupling yield is checked by means of the Kaiser test (Anal. Biochem. 34 (1970), 595). After the coupling the Fmoc group is cleaved off by incubation with 20% piperidine in dimethylformamide for 10–20 min. at room temperature. The loading of the resin is determined after each piperidine cleavage by means of UV absorption of the released fulvene group. After complete synthesis of the peptide the degree of loading is still 0.43 mmol/g.

The peptide is released from the resin by incubation with 200 ml trifluoroacetic acid, 20 ml ethanedithiol, 20 ml m-cresol and 10 ml water for 30 min. at room temperature. The reaction solution is subsequently evaporated several times with toluene while excluding air and then the peptide is precipitated with peroxide-free diethyl ether.

For the purification the crude material obtained is purified under a $N_2$ atmosphere via a Sephadex-G10 column. 2.4 g material with a purity of 54% according to RP-HPLC are obtained after lyophilization.

For the further purification, 400 mg of this peptide is purified by a preparative RP-HPLC column (40 mm×250 mm C18 material, 5 µm, 300 Å) with a water/trifluoroacetic acid to acetonitrile/trifluoroacetic acid gradient (buffer A: 0.1% trifluoroacetic acid in water, buffer B: 0.1% trifluoroacetic acid in water/acetonitrile 60:40 from 0% B to 100% B in 60 min.). After lyophilization 97 mg white material is obtained with a purity of 97.2% according to HPLC. The identity of the peptide obtained is checked by means of FAB-MS.

EXAMPLE 2

Biotinylation of the Peptide

For the biotinylation of one mole equivalent of the peptide antigen obtained according to example 1, the peptide is dissolved at a concentration of 5 mg/ml in argon-saturated potassium phosphate buffer (0.1 mol/l pH 8.0) 3 equivalents D-biotinyl-ε-aminocaproic acid-N-hydroxysuccinimide ester (1 µmol dissolved in 5 µl argon-saturated dimethylformamide) are added and it is incubated for 2 hours at room temperature while stirring and under an argon atmosphere. As soon as the initial products have decreased to less than 5% as monitored by analytical RP-HPLC, the reaction mixture is applied directly to a preparative RP-HPLC column and the product is purified by means of a 0.1 % trifluoroacetic acid/water to 0.1% trifluoroacetic acid/acetonitrile gradient (0% to 100% acetonitrile in 90 min. ). The product is concentrated and lyophilized, the yield is between 40 and 90%. The purity of the material obtained is determined by means of HPLC, capillary electrophoresis and TLC, the identity is determined by FAB-MS and TLC using specific staining reagents (p-dimethylaminocinnamaldehyde for the content of biotin) and the assay is determined by means of microanalysis.

EXAMPLE 3

Affinity Chromatographic Purification of Antisera Against Lp(a)

The immunoabsorbent is produced as described by Chersi et al., (J. Immunol. Meth. 122 (1989), 285–289). For this Sepharose-AH (3 ml packed gel in 6 ml PBS) is treated with maleimidobenzoyl-N-hydroxysuccinimide ester (MBS, 5 mg/ml in dimethylformamide) for 2 hours at room temperature while mixing carefully. Excess MBS is subsequently removed by centrifugation at 2000 g for 15 min. at 4° C. In order to wash the gel material, it is resuspended in PBS and again centrifuged. These washing cycles are repeated several times. After the last centrifugation step, 2 mg of an equimolar mixture of the peptides having the sequences shown in SEQ ID NO 1–8 in 4 ml PBS are added to the gel, carefully mixed and incubated for 60 min at room temperature. Mercaptoethanol is subsequently added to the suspension to a final concentration of 10 mmol/l, it is again incubated for 30 minutes, dispensed into a small column and washed with PBS/10 mmol/l mercaptoethanol. Before purifying the antibodies, the gel material is subjected to the following washing cycle. It is washed with at least 3 column volumes PBS, 0.5 mmol/l NaCl/0.05% Tween 20, 30 mmol/l NaCl, 0.2 mol/l glycine, pH 2.6 and 30 mmol/l NaCl. Subsequently the gel material is equilibrated with PBS, pH 7.0 and the serum to be purified which contains the antibody is applied to the column. After washing steps with PBS, 0.5 mol/l NaCl/0.05% Tween 20 and 30 mmol/l NaCl, the bound antibody is eluted with 0.2 mol/l glycine, pH 2.6 and directly afterwards dialysed against PBS at 4° C.

EXAMPLE 4

Determination of the Specificity of the Immunoadsorptively Purified Antibodies

The specificity of the antibodies obtained according to example 3 is determined by means of a sandwich assay. The following reagents are used for this:

Reagent 1:

Biotinylated peptide prepared according to example 1 (0.2 µg/ml)

40 mmol/l phosphate buffer pH 7.0, 0.9% sodium chloride

10% BSA.

Reagent 2:

20 mU/ml peroxidase-labelled Fab fragments against sheep immunoglobulin G (Boehringer Mannheim GmbH, Cat. No. 1301 977)

40 mmol/l phosphate buffer pH 7.0

0.5% Tween 20

0.2% BSA 0.2% bovine immunoglobulin (Sigma, Cat. No. I 5506)

For the experimental procedure, 1 ml reagent 1 and 10 µl of the antibody solution to be tested diluted 1:100 are pipetted into streptavidin-coated polystyrene tubes (produced according to example 1 of EP-A 344 578) and incubated for 1 hour at room temperature. The tubes are then washed three times with normal tap water and subsequently incubated with 1 ml reagent 2 for 1 hour at room temperature and then again washed three times with tap water. After addition of 1 ml ABTS® in 100 mmol/l phosphate-citrate buffer pH 4.4 containing 3.2 mmol/l sodium perborate (Boehringer Mannheim GmbH, Cat. No. 746407) and incubating for 60 min. at room temperature, the binding of the labelled Fab fragments is then determined by measuring the absorbance at 420 nm. The following table shows the reactivity of 8 examined antisera with the peptides of the sequences shown in SEQ ID NO 1–8. In this case a signal which has a value that is 3 standard deviations higher than the mean value of 10 negative control sera is classified as positive.

TABLE 1

| Antiserum | SEQ ID NO: | | | | | | | |
|---|---|---|---|---|---|---|---|---|
| | 1 | 2 | 3 | 4 | 5 | 6 | 7 | 8 |
| a | + | + | + | + | + | + | + | − |
| b | + | − | − | − | + | − | + | − |
| c | − | − | + | − | − | − | − | − |
| d | − | − | − | + | − | − | − | − |
| e | − | − | − | − | + | − | − | − |
| f | + | + | + | − | − | − | − | − |
| g | − | − | − | − | − | − | + | + |
| h | + | − | − | + | − | − | + | + |

EXAMPLE 5

Cross-Reactivity of the Immunoadsorptively Purified Antibodies

For the determination of the cross-reactivity of antiserum a (see example 4, Table 1), the sandwich immunoassay described in example 4 is carried out in the presence of different concentrations of Lp(a), LDL and plasminogen (concentrations see Table 2). In this process these free antigens which were added compete with the immobilized biotinylated peptides for binding to the antiserum so that the binding of the antiserum to the solid phase and hence the signal strength increases to an extent which corresponds to the reactivity of the added free antigens with the antiserum. Thus the more free antigen is needed to reduce the obtained signal, the smaller is the reactivity of the antiserum with this antigen. Antiserum a is examined in this manner before and after the affinity chromatographic purification according to example 3. The cross-reactivity of antiserum a towards LDL and plasminogen can be significantly reduced by the affinity chromatographic purification as shown in Table 2.

TABLE 2

| Substance/concentration (µmol/l) | Signal | |
|---|---|---|
| | before purification | after purification |
| Lp(a) | | |
| 0 | 287 | 241 |
| 0.5 | 270 | 228 |
| 1.0 | 237 | 174 |
| 2.0 | 77 | 40 |
| 3.0 | 12 | 8 |
| LDL | | |
| 0 | 287 | 241 |
| 2.0 | 268 | 240 |
| 5.0 | 232 | 241 |
| 10.0 | 140 | 240 |
| 20.0 | 66 | 239 |
| 40.0 | 7 | 242 |

TABLE 2-continued

| Substance/concen- | Signal | |
|---|---|---|
| tration (μmol/l) | before purification | after purification |
| 100.0 | 0 | 235 |
| 200.0 | 0 | 218 |
| 500.0 | 0 | 104 |
| 1000.0 | 0 | 29 |
| 2000.0 | 0 | 0 |
| Plasminogen | | |
| 0 | 287 | 241 |
| 2.0 | 274 | 240 |
| 5.0 | 260 | 242 |
| 10.0 | 226 | 243 |
| 20.0 | 149 | 242 |
| 40.0 | 62 | 241 |
| 100.0 | 1 | 239 |
| 200.0 | 0 | 230 |
| 500.0 | 0 | 172 |
| 1000.0 | 0 | 53 |
| 2000.0 | 0 | 7 |

EXAMPLE 6

Agglutination Test for the Immunological Determination of Lp(a)

Lp(a) is determined in a homogeneous immunoassay. Reagents with the following composition are used for the test:

Reagent 1:

monoclonal antibody against peptide 1 (75 μg/ml, Boehringer Mannheim GmbH, Cat. No. 1411 012)

polystreptavidin (20 μg/ml)

20 mmol/l MES, pH 6.0

225 mmol/l NaCl 4.5% PEG 6000

0.75% Brij 35

0.1% $NaN_3$

Reagent 2:

20 mmol/l MES, pH 6.0

150 mmol/l NaCl 6.0% PEG 6000

0.5% Brij 35

0.1% $NaN_3$ biotinylated peptide (2 μg/ml, see example 2)

The measurements are carried out on a Hitachi 704 at 37° C. 350 μl reagent 1 and 10 μl sample are incubated for 5 min in a cuvette. Subsequently 70 μl reagent 2 is added by pipette and incubated for 5 min. and the change in absorbance is determined at 340 nm. The measured turbidity is compared with the turbidity which is obtained by addition of known amounts of a Lp(a) standard and the amount of Lp(a) in the sample to be analysed is determined from the comparison.

We claim:

1. A lipoprotein (a) peptide comprising a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8, wherein said peptide has a random coil structure which produces a negative band between 190 and 200 nm when examined using CD spectroscopy, and wherein said peptide has the same specificity or antigenicity as a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 AND SEQ ID NO: 8.

2. The peptide according to claim 1, wherein said peptide is less than 50 amino acids in length.

3. The peptide according to claim 2, wherein said peptide is 7–20 amino acids in length.

4. The peptide according to claim 1, wherein said peptide is synthetically produced.

5. The peptide according to claim 4, wherein said peptide is produced by means of fluorenyl-oxycarbonyl solid phase synthesis.

6. A lipoprotein (a) peptide comprising a part of a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8, wherein said peptide has a random coil structure which produces a negative band between 190 and 200 nm when examined using CD spectroscopy, wherein said peptide has the same specificity or antigenicity as a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 AND SEQ ID NO: 8 and wherein said part of said sequence is at least 4 amino acids in length.

7. A standard for use in an immunological test for the quantitative determination of Lp(a), comprising a uniform composition of lipoprotein (a) peptides comprising a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8, wherein said peptide has a random coil structure which produces a negative band between 190 and 200 nm when examined using CD spectroscopy, and wherein said peptide has the same specificity or antigenicity as a peptide selected from the group consisting of SEQ ID NO: 1, SEQ ID NO: 2, SEQ ID NO: 3, SEQ ID NO: 4, SEQ ID NO: 5, SEQ ID NO: 6,SEQ ID NO: 7 AND SEQ ID NO: 8.

8. A hapten for use in a competitive immunological test, comprising a lipoprotein (a) peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8, wherein said peptide has a random coil structure which produces a negative band between 190 and 200 nm when examined using CD spectroscopy, wherein said peptide has the same specificity or antigenicity as a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 AND SEQ ID NO: 8 and wherein said peptide is bound to a solid phase.

9. An Lp(a) hapten for use in an agglutination test, comprising a lipoprotein (a) peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8, wherein said peptide has a random coil structure which produces a negative band between 190 and 200 nm when examined using CD spectroscopy, wherein said peptide has the same specificity or antigenicity as a peptide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 AND SEQ ID NO: 8, wherein said peptide is bound to a carrier and an agglutinate forms after incubation of the peptide with an antibody against said peptide, and wherein formation of said agglutinate is decreased when free Lp(a) is present.

* * * * *

UNITED STATES PATENT AND TRADEMARK OFFICE
CERTIFICATE OF CORRECTION

PATENT NO. : 5,486,476

DATED : January 23, 1996

INVENTOR(S) : BURNS et al.

It is certified that error appears in the above-indentified patent and that said Letters Patent is hereby corrected as shown below:

On the title page,

Item [30] please delete "43 04 638.4" insert therefor -- 43 03 638.4 --

Item [30], line 2, insert therefor -- No. 43 10 516.5, country Germany, date March 31, 1993 --

Item [75], line 1, delete "Wolf-Deiter Engel," insert therefor -- Wolf-Dieter Engel, --

Signed and Sealed this

Twenty-ninth Day of April, 1997

*Attest:*

BRUCE LEHMAN

*Attesting Officer*    Commissioner of Patents and Trademarks